United States Patent
Wachter et al.

(10) Patent No.: US 6,589,945 B1
(45) Date of Patent: Jul. 8, 2003

(54) USE OF STEROLSULFATES AS ACTIVE SUBSTANCES FOR PRODUCING MEANS TO INHIBIT SERIN PROTEASES

(75) Inventors: Rolf Wachter, Duesseldorf (DE); Holger Tesmann, Juechen (DE); Ansgar Behler, Bottrop (DE); Karl-Heinz Maurer, Erkrath (DE)

(73) Assignee: Cognis Deutschland GmbH & Co. KG, Duesseldorf (DE)

( * ) Notice: Subject to any disclaimer, the term of this patent is extended or adjusted under 35 U.S.C. 154(b) by 0 days.

(21) Appl. No.: 09/284,670

(22) PCT Filed: Oct. 8, 1997

(86) PCT No.: PCT/EP97/05524

§ 371 (c)(1),
(2), (4) Date: Apr. 16, 1999

(87) PCT Pub. No.: WO98/17244

PCT Pub. Date: Apr. 30, 1998

(30) Foreign Application Priority Data

Oct. 17, 1996 (DE) .......................... 196 42 872

(51) Int. Cl.⁷ .................. A61K 7/48; A61K 31/56; A61K 7/00; A61K 31/565
(52) U.S. Cl. ............ 514/169; 514/178; 514/182; 552/540; 552/544
(58) Field of Search ................ 514/169, 178, 514/182; 552/540, 544

(56) References Cited

U.S. PATENT DOCUMENTS

| | | | |
|---|---|---|---|
| 3,547,828 A | 12/1970 | Mansfield et al. | 252/351 |
| 3,707,535 A | 12/1972 | Lew | 260/210 |
| 3,772,269 A | 11/1973 | Lew | 260/210 |
| 3,839,318 A | 10/1974 | Mansfield | 260/210 |
| 4,172,887 A | 10/1979 | Vanlerberghe et al. | 424/70 |
| 4,349,669 A | 9/1982 | Klahr et al. | 536/127 |
| 5,202,126 A | 4/1993 | Perrier et al. | 424/450 |

FOREIGN PATENT DOCUMENTS

| | | |
|---|---|---|
| DE | 11 65 574 | 8/1960 |
| DE | 19 43 689 | 3/1970 |
| DE | 20 36 472 | 2/1971 |
| DE | 20 24 051 | 12/1971 |
| DE | 30 01 064 | 7/1981 |
| EP | 0 077 167 | 4/1983 |
| EP | 0 723 775 | 7/1996 |
| FR | 22 52 840 | 12/1978 |
| GB | 962919 | 7/1964 |
| GB | 1 333 475 | 10/1973 |
| JP | 60 161911 | 8/1985 |
| JP | 61 260004 | 11/1986 |
| JP | 5 51315 | 3/1993 |
| WO | WO88/01274 | 2/1988 |
| WO | WO89/01327 | 2/1989 |
| WO | WO90/01323 | 2/1990 |

OTHER PUBLICATIONS

1987.*
Cosmetics & Toiletries vol. 111, (1996) pp. 51–55.
J.Am.Chem.Soc. vol. 63, (1941) p. 1259.
J.Falbe "Surfactants in Consumer Products" (1987) pp. 54–124.
Majewska et al. [CA 114:17712 abstract of Eur. J. Pharmacol. Mol. Pharmacol. Sect. (1990), 189(4–5), 307–15.*
Demirgoren et al. [CA 115:270905 abstract of Neuroscience (Oxford) (1991), 45(1), 127–135].*

* cited by examiner

*Primary Examiner*—Sabiha Qazi
(74) *Attorney, Agent, or Firm*—John E. Drach; Steven J. Trzaska; Glenn E. Murphy

(57) ABSTRACT

A process for treating human skin by inhibiting serine protease formation involving contacting the skin with a composition containing a sterol sulfate.

4 Claims, No Drawings

USE OF STEROLSULFATES AS ACTIVE SUBSTANCES FOR PRODUCING MEANS TO INHIBIT SERIN PROTEASES

This application is a 371 of PCT/EP97/05524 filed Oct. 8, 1997.

FIELD OF THE INVENTION

This invention relates to the use of sterol sulfates as active principles for controlling wrinkling of the skin and skin diseases, for example psoriasis and UV erythemas.

DISCUSSION OF THE RELATED ART

Wrinkling of the skin with age is caused by the degradation of various macromolecules, such as for example elastin and collagen, for which elastases in the stratum corneum are responsible. Various inflammatory skin diseases, for example psoriasis or UV erythrema, can also be attributed to a high concentration of elastase in the upper layers of the skin [cf. R. Voegeli et al in Cosm. Toil. 111, 51 (1996)].

In general, wrinkling of the skin is not counteracted by physiologically active principles, but rather by cosmetic compositions. Many so-called anti-aging products contain liposomes charged with water or aqueous active principles which enter the epidermis through the fatty layer of the skin, gradually dissolve there, fill the wrinkles through the continuous release of water and regulate the moisture content of the skin. However, this effect has nothing to do with fighting the causes, but is merely a so-called repair effect which, moreover, only lasts for a short time.

In contrast to this purely cosmetic application, cytostatic agents for example, such as selenium sulfide, cadmium sulfide, zinc pyrithione or corticosteroids, are used in the treatment of psoriasis, their medicinal effect being attributable, for example, to a reduction in mitose activity in the basal membrane. On account of their well-known side effects, however, these substances should not be used over long periods. In addition, psoriasis can be treated but not cured by antiseptic agents, for example selenium oxide, salicylic acid, pyrithione derivatives, hexachlorophene or quaternary ammonium compounds, or by cell-dissolving and defatting agents such as, for example, benzoyl peroxide or tar extracts.

Accordingly, very difficult solutions are known from the prior art for smoothing the skin and strengthening the barrier function either from the cosmetic or from the medicinal standpoint. Unfortunately, they solve only part of the problem and, in addition, can be accompanied by strong side effects. Accordingly, the complex problem addressed by the present invention was to provide active principles which could be used both against wrinkling of the skin (cosmetic effect) and against skin diseases (medicinal effect) and which, at the same time, would have high dermatological and toxicological compatibility.

DESCRIPTION OF THE INVENTION

The present invention relates to the use of sterol sulfates as active principles for the production of compositions for inhibiting serine proteases, preferably elastases.

It has surprisingly been found that sterol sulfates deactivate serine proteases in general and elastases in particular and thus slow down the degradation of macromolecules, such as elastin, collagen, etc., in the connective tissue. In this way, wrinkling of the skin with age is reduced. In addition, the topical application of sterol sulfates ensures a high concentration of the active principle in the stratum corneum so that the cohesion of the corneocytes is increased and the upper layers are thickened. This effect is particularly important in the case of damaged skin because the stratum corneum is unable to perform its barrier function if the skin is damaged. The invention also includes the observation that sterol sulfates, by inhibiting elastase, also lead to the prevention or reduction of inflammatory reactions and may therefore be used for treating skin diseases. Finally, sterol sulfates which occur in concentrations of up to 4% by weight in the upper layers of the stratum corneum are known to be highly compatible with the skin and toxicologically safe.

Sterol sulfates

Sterol sulfates are known substances which may be prepared, for example, by sulfation of sterols with a complex of sulfur trioxide and pyridine in benzene [cf. J. Am. Chem. Soc. 63, 1259 (1941)]. Sterols—which may be used as starting materials for the production of sterol sulfates—are understood to be steroids which contain only a hydroxyl group but no other functional groups at C-3. Formally, therefore, they are alcohols which would explain why this group of compounds is sometimes also referred to as sterols. Generally, sterols contain 27 to 30 carbon atoms and one double bond in the 5/6 position and optionally in the 7/8, 8/9 or other positions. Besides these unsaturated species, however, other suitable starting materials are the saturated compounds obtainable by hydrogenation. Typical examples of suitable sterol sulfates are those based on zoosterols, for example animal cholesterol, lanosterols from wool fat, spongosterols from sponges of stellasterols from starfish. However, phytosterol sulfates, for example those based on ergosterols, campesterols, stigmasterols and sitosterols, are preferably used by virtue of the lighter color of the sulfation products. The sterol sulfates may be used in the form of alkali metal and/or alkaline earth metal salts, ammonium, alkylammonium, alkanolammonium and/or glucammonium salts. They are generally used in the form of the sodium salts.

The sterol sulfates may be marketed in pure solid form. However, they may also be marketed in the form of solutions in suitable solvents, for example propylene glycol or butylene glycol, or as compounds, for example together with fatty alcohol ether sulfates, as raw materials for the production of cosmetic or pharmaceutical compositions. In these concentrated formulations, the sterol sulfate content may be in the range from 0.1 to 10% by weight and is preferably is in the range from 1 to 5% by weight and more preferably in the range from 2 to 8% by weight.

Commercial Applications

According to the invention, the sterol sulfates may be used as active principles for the production of cosmetic and/or pharmaceutical compositions. Typical examples of such compositions are skin-care products such as, for example, anti-wrinkle cremes, anti-cellulite cremes or sun protection lotions and ointments for the treatment of skin diseases such as, for example, cradle cap, psoriasis, seborrhoeic dermatitis, seborrhoea sicca, seborrhoea oleosa, psoriasis vulgaris, ichtyoses or UV erythemas. The sterol sulfates are normally used in quantities of 0.0001 to 5% by weight, preferably in quantities of 0.001 to 1% by weight and more preferably in quantities of 0.01 to 0.1% by weight, based on the particular composition.

The compositions may contain small quantities of anionic, nonionic, cationic and/or amphoteric or zwitterionic surfactants compatible with the other ingredients. Typical examples of anionic surfactants are soaps, alkyl benzenesulfonates, alkanesulfonates, olefin sulfonates, alkylether sulfonates, glycerol ether sulfonates, α-methyl ester sulfonates, sulfofatty acids, alkyl sulfates, fatty alcohol ether sulfates, glycerol ether sulfates, hydroxy mixed ether sulfates, monolyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids such as, for example, acyl lactylates, acyl tartrates, acyl glutamates and acyl aspartates, alkyl oligo-clugocide sulfates, protein fatty acid condensates (particularly wheat-based vegetable products) and alkyl (ether) phosphates. If the anionic surfactants contain polyglycol ether chains, they may have a conventional homolog distribution although they preferably have a narrow-range homolog distribution. Typical examples of nononic surfactants are fatty alcohol polyglycol ethers, alkylphenyl polyglycol ethers, fatty acid polyglycol esters, fatty acid amide polyglycol ethers, fatty amine polyglycol ethers, alkoxylated triglycerides, mixed ethers and mixed formals, alk(en)yl oligoglycosides, fatty acid N-alkyl glucamides, protein hydrolyzates (particularly wheat-based vegetable products), polyol fatty acid esters, sugar esters, sorbitan esters, polysorbates and amine oxides. If the nonionic surfactants contain polyglycol ether chains, they may have a conventional homolog distribution, although they preferably have a narrow-range homolog distribution. Typical examples of cationic surfactants are quaternary ammonium compounds and esterquats, more particularly quaternized fatty acid trialkanolamine ester salts. Typical examples of amphoteric or zwitterionic surfactants are alkylbetaines, alkylaminodbetaines, aminopropionates, aminoglycinates, imidazolinium betaines and sulfobetaines. The surfactants mentioned are all known compounds. Information on their structure and production can be found in relevant synoptic works, cf. for example J. Falbe (ed.), "Surfactants in Consumer Products", Springer Verlag, Berlin, 1987, pages 54 to 124 or J. Falbe (ed.), "Katalysatoren, Tenside and Mineral öladditive (Catalysts, Surfactants and Mineral Oil Additives) ", Thieme Verlag, Stuttgart, 1978, pages 123–217.

The compositions may contain oils, emulsifiers, superfatting agents, stabilizers, waxes, consistency promoters, thickeners, cationic polymers, silicone compounds, biogenic agents, antidandruff agents, film formers, preservatives, hydroptropes, solubilizers, UV filters, dyes and fragrances as further auxiliaries and additives.

Suitable oils are, for example, Guerbet alcohols based on $C_{6-18}$ and preferably $C_{8-10}$ fatty alcohols, esters of linear $C_{6-20}$ fatty acids with linear $C_{6-20}$ fatty alcohols, esters of branched $C_{6-13}$ carboxylic acids with linear $C_{6-20}$ fatty alcohols, esters of linear $C_{6-18}$ fatty acids with branched alcohols, more particularly 2-ethyl hexanol, esters of linear and/or branched fatty acids with polyhydric alcohols (for example dimer diol or trimer triol) and/or Guerbet alcohols, triglycerides based on $C_{6-10}$ fatty acids, vegetable oils, branched primary alcohols, substituted cyclohexanes, Guerbet carbonates, dialkyl ethers, silicone oils and/or aliphatic or naphthenic hydrocarbons.

Suitable emulsifiers are, for example, nonionic surfactants from at least one of the following groups:

(b1) adducts of 2 to 30 moles of ethylene oxide and/or 0 to 5 moles of propylene oxide with linear fatty alcohols containing 8 to 22 carbon atoms, with fatty acids containing 12 to 22 carbon atoms and with alkylphenols containing 8 to 15 carbon atoms in the alkyl group;

(b2) $C_{12/18}$ fatty acid monoesters and diesters of adducts of 1 to 30 moles of ethylene oxide with glycerol;

(b3) glycerol monoesters and diesters and sorbitan monoesters and diesters of saturated and unsaturated fatty acids containing 6 to 22 carbon atoms and ethylene oxide adducts thereof;

(b4) alkyl mono- and oligoglycosides containing 8 to 22 carbon atoms in the alkyl group and ethoxylated analogs thereof;

(b5) adducts of 15 to 60 moles of ethylene oxide with castor oil and/or hydrogenated castor oil;

(b6) polyol esters and, in particular, polyglycerol esters such as, for example, polyglycerol polyricinoleate or polyglycerol poly-12-hydroxystearate. Mixtures of compounds from several of these classes are also suitable;

(b7) adducts of 2 to 15 moles of ethylene oxide with castor oil and/or hydrogenated castor oil;

(b8) partial esters based on linear, branched, unsaturated or saturated $C_{12/22}$ fatty acids, ricinoleic acid and 12-hydroxystearic acid and glycerol, polyglycerol, pentaerythritol, dipentaerythritol, sugar alcohols (for example sorbitol) and polyglucosides (for example cellulose);

(b9) trialkyl phosphates;

(b10) wool wax alcohols;

(b11) polysiloxane/polyalkyl polyether copolymers and corresponding derivatives;

(b12) mixed esters of pentaerythritol, fatty acids, citric acid and fatty alcohol according to DE-PS 11 65 574 and (b13) polyalkylene glycols.

The addition products of ethylene oxide and/or propylene oxide with fatty alcohols, fatty acids, alylphenols, glycerol monoesters and diesters and sorbitan monoesters and diesters of fatty acids or with castor oil are known commercially available products. They are homolog mixtures of which the average degree of alkoxylation corresponds to the ratio between the quantities of ethylene oxide and/or propylene oxide and substrate with which the addition reaction is carried out. $C_{12/18}$ fatty acid monoesters and diesters of adducts of ethylene oxide with glycerol are known as refatting agents for cosmetic formulations from DE-PS 20 24 051.

$C_{8/18}$ alkyl mono- and oligoglycosides, their production and their use as surfactants are known, for example, from U.S. Pat. No. 3,839,318, U.S. Pat. No. 3,707,535, U.S. Pat. No. 3,547,828, DE-OS 19 43 689, DE-OS 20 36 472 and DE-A1 30 01 064 and also from EP-A 0 077 167. They are produced in particular by reacting glucose or oligosaccharides with primary $C_{8/18}$ alcohols. So far as the glycoside unit is concerned, both monoglycosides in which a cyclic sugar unit is attached to the fatty alcohol by a glycoside bond and oligomeric glycosides with a degree of oligomerization of preferably up to about 8 are suitable. The degree of oligomerization is a statistical mean value on which the homolog distribution typical of such technical products is based.

In addition, zwitterionic surfactants may be used as emulsifiers. Zwitterionic surfactants are surface-active compounds which contain at least one quaternary ammonium group and at least one carboxylate and one sulfonate group in the molecule. Particularly suitable zwitterionic surfactants are the so-called betaines, such as the N-alkyl-N,N-dimethyl ammonium glycinates, for example cocoalkyl dimethyl ammonium glycinate, N-acylaminopropyl-N,N-dimethyl ammonium glycinates, for example cocoacylaminopropyl dimethyl ammonium glycinate, and 2-alkyl-3-carboxymethyl-3-hydroxyethyl imidazolines containing 8 to 18 carbon atoms in the alkyl or acyl group and cocoacylaminoethyl hydroxyethyl carboxymethyl glycinate. The fatty acid amide derivative known under the CTFA name of Cocamidopropyl Betaine is particularly preferred. Amphyolytic surfactants are also suitable emulsifiers. Ampholytic surfactants are surface-active compounds which, in addition to a $C_{8/18}$ alkyl or acyl group, contain at least one free amino group and at least one —COOH— or —$SO_3$-group in the molecular and which are capable of forming inner salts. Examples of suitable ampholytic surfactants are N-alkyl glycines, N-alkyl propionic acids, N-alkylaminobutyric acids, N-alkyliminodipropionic acids, N-hdyroxyethyl-N-alkylamidopropyl glycines, N-alkyl taurines, N-alkyl sarcosines, 2-alkylaminopropionic acids and alkylaminoacetic acids containing around 8 to 18 carbon atoms in the alkyl group. Particularly preferred ampholytic surfactants are N-cocoalkylaminopropionate, cocoacylaminoethyl aminopropionate and $C_{12/18}$ acyl sarcosine. Besides ampholytic emulsifiers, quaternary emulsifiers may also be used, those of the esterquat type, especially methyl-quaternized difatty acid triethanolamine ester salts, being particularly preferred.

Superfatting agents may be selected from such substances as, for example, lanolin and lecithin and also polyethoxylated or acylated lanolin and lecithin derivatives, polyol fatty acid esters, monoglycerides and fatty acid alkanolamides, the fatty acid alkanolamides also serving as foam stabilizers. The consistency promoters mainly used are fatty alcohols containing 12 to 22 and preferably 16 to 18 carbon atoms. A combination of these substances with alkyl oligoglucosides and/or fatty acid N-methyl glucamides of the same chain length and/or polyglycerol poly-12-hydroxystearates is preferably used. Suitable thickeners are, for example, polysaccharides, more especially xanthan gum, guar-guar, agar-agar, alginates and tyloses, carboxymethyl cellulose and hydroxyethyl cellulose, also relatively high molecular weight polyethylene glycol monoesters and diesters of fatty acids, polyacrylates, polyvinyl alcohol and polyvinyl pyrrolidone, surfactants such as, for example, ethoxylated fatty acid glycerides, esters of fatty acids with polyols, for example pentaerythritol or trimethylol propane, narrow-range fatty alcohol ethoxylates or alkyl oligoglucosides and electrolytes, such as sodium chloride and ammonium chloride.

Suitable cationic polymers are, for example, cationic cellulose derivatives, cationic starch, copolymers of diallyl ammonium salts and acrylamides, quaternized vinyl pyrrolidone/vinyl imidazole polymers such as, for example, Luviquat® (BASF AG, Ludwigshafen, FRG), condensation products of polyglycols and amines, quaternized collagen polypeptides such as, for example, Lauryldimonium Hydroxypropyl Hydrolyzed Collagen (Lamequat®L, Gr ünau GmgH), quaternized wheat polypeptides, polyethyleneimine, cationic silicone polymers such as, for example, Amidomethicone or Dow Corning, Dow Corning Co., USA, copolymers of adipic acid and dimethylaminohydroxypropyl diethylenetriamine (Cartaretine®, Sandoz AG, CH), polyaminopolyamides as described, for example, in FR-A 2 252 840 and crosslinked water-soluble polymers thereof, cationic chitin derivatives such as, for example, quaternized chitosan, optionally in microcrystalline distribution, condensation products of dihaloalkyls, for example dibromobutane, with bis-dialylamines, for example, bis-dimethylamino-1,3-propane, cationic guar gum such as, for example, Jaguar® CBS, Jaguar® C-17, Jaguar® C-16 of Celanese, USA, quaternized amonium salt polymers such as, for example, Mirapol® A-15, Mirapol® AD-1, Mirapol® AZ-1 of Miranol, USA.

Suitable silicone compounds are, for example, dimethyl polysiloxanes, methylphenyl polysiloxanes, cyclic silicones and amino-, fatty acid-, alcohol-, polyether-, epoxy-, fluorine- and/or alkoxy-modified silicone compounds which may be both liquid and resin-like at room temperature. Typical examples of fats are glycerides while suitable waxes are inter alia beeswax, paraffin wax or microwaxes, optionally in combination with hydrophilic waxes, for example cetyl stearyl alcohol. Suitable pearlescent waxes are, in particular, mono- and difatty acid esters of polyalkylene glycols, partial glycerides and esters of fatty alcohols with polybasic carboxylic acids or hydroxycarboxylic acids. Metal salts of fatty acids such as, for example, magnesium, aluminium and/or zinc stearate may be used as stabilizers. In the context of the invention, biogenic agents are, for example, bisabolol, allantoin, phytantriol, panthenol, AHA acids, plant extracts and vitamin complexes. Climbazol, octopirox and zinc pyrthione may be used as antidandruff agents. Typical film formers are, for example, chitosan, microcrystalline chitosan, quaternized chitosan, polyvinyl pyrrolidone, vinyl pyrrolidone/vinyl acetate copolymers, polymers o the acrylic acid series, quaternary celllose derivatives, collagen, hyaluronic acid and salts thereof and similar compounds. In addition, hydrotropes such as, for example, ethanol, isopropyl alcohol, propylene glycol or glucose may be used to improve flow behavior. Suitable preservatives are, for example, phenoxyethanol, formaldehyde solution, parabens, pentanediol or sorbic acid.

Typical examples of UV filters are 4-aminobenzoic acid and esters and derivatives thereof (for example 2-ethylhexyl-p-dimethylaminobenzoate of p-dimethylaminobenzoic acid octyl ester), methoxycinnamic acid and derivatives thereof (for example 4-methoxycinnamic acid-2-ethylhexyl ester), benzophenones (for example oxybenzone, 2-hydroxy-4-methoxybenzophenone), dibenzoyl methanes, salicylates esters, 2-phenyl benzimidazole-5-sulfonic acid, 1-(4-tert.butylphenyl)-3-(4'-methoxyphenyl)propane-1,3-dione, 3-(4'-methyl)-benzylidene-bornan-2-one, methyl methyl-benzylidene camphor and the like. Other suitable UV filters are finely disperse metal oxides and salts, for example titanium dioxide, zinc oxide, iron oxide, aluminium oxide, cerium oxide, zirconium oxide, silicates (talcum) and barium sulfate. Finally, secondary light filters of the antioxidant type, such as Superoxid-Dismutase, tocopherols (vitamin E) and ascorbic acid (vitamin C), may also be used.

The dyes used may be selected from any of the substances which are approved and suitable for cosmetic purposes, as listed for example in the publication "Kosmetische F ̈arbemittel" of the Farbstoffkommission der Deutschen Forschungsgemeinschaft, published by Verlag Chemie, Weinheim, 1984, pages 81–106. These dyes are typically used in concentrations of 0.001 to 0.1% by weight, based on the mixture as a whole.

The total content of auxiliaries and additives may be from 1 to 50% by weight and is preferably from 5 to 40% by weight, based on the composition. The compositions may be produced by standard cold or hot processes and are preferably produced by the phase inversion temperature method.

EXAMPLES

The elastase-inhibiting effect of various sterol derivatives was investigated in the concentration range from 2.5 to 1000 ppm. The results are set out in Table 1. Examples 1 and 2 correspond to the invention while Examples C1 to C3 are intended for comparison.

TABLE 1

| | Elastase-inhibiting effect [%-rel] at various concentrations (2.5 to 1000 ppm) | | | | |
|---|---|---|---|---|---|
| Ex. Inhibitor | 2.5 ppm | 5 ppm | 12.5 ppm | 500 ppm | 1000 ppm |
| 1 Cholesterol sulfate, sodium salt | 49 | 92 | 100 | — | — |
| 2 Phytosterol sulfate, sodium salt | 31 | 64 | 98 | — | — |
| C1 Cholesterol acetate | 0 | 0 | 0 | 33 | 59 |
| C2 Phytosterol succinate | 0 | 0 | 0 | 0 | 0 |
| C3 Phytosterol phosphate | 0 | 0 | 0 | 0 | 30 |

What is claimed is:

1. A process for treating human skin by inhibiting serine protease formation comprising contacting the skin with a composition consisting essentially of from about 0.01 to 0.1% by weight, based on the weight of the composition, of a sterol sulfate.

2. The process of claim 1 wherein the sterol sulfate is present in the composition in salt form.

3. A topical cosmetic composition comprising from about 0.01 to 0.1% by weight, based on the weight of the composition, of a sterol sulfate.

4. A topical pharmaceutical composition comprising from about 0.01 to 0.1% by weight, based on the weight of the composition, of a sterol sulfate.

* * * * *